United States Patent
Cui et al.

(10) Patent No.: US 6,887,488 B2
(45) Date of Patent: May 3, 2005

(54) NANO-CALCIUM PHOSPHATES/COLLAGEN BASED BONE SUBSTITUTE MATERIALS

(75) Inventors: Fuzhai Cui, Beijing (CN); Shuming Zhang, Beijing (CN); Wei Zhang, Beijing (CN); Qiang Cai, Beijing (CN); Qingling Feng, Beijing (CN)

(73) Assignee: Tsinghua University, Beijing (CN)

( * ) Notice: Subject to any disclaimer, the term of this patent is extended or adjusted under 35 U.S.C. 154(b) by 390 days.

(21) Appl. No.: 09/845,724

(22) Filed: May 2, 2001

(65) Prior Publication Data

US 2002/0018797 A1 Feb. 14, 2002

(30) Foreign Application Priority Data

May 19, 2000 (CN) .......................................... 00107493

(51) Int. Cl.⁷ ........................... A61F 2/00; C12N 11/14; C12N 11/02; C12N 5/06; C12N 5/08
(52) U.S. Cl. ...................... 424/426; 424/93.7; 435/176; 435/177; 435/395
(58) Field of Search ................................ 424/426, 93.7; 435/176, 177, 395

(56) References Cited

U.S. PATENT DOCUMENTS

| | | | |
|---|---|---|---|
| 5,626,861 A | 5/1997 | Laurencin et al. | 424/426 |
| 6,013,591 A | 1/2000 | Ying et al. | 501/1 |
| 6,331,312 B1 * | 12/2001 | Lee et al. | 424/426 |

FOREIGN PATENT DOCUMENTS

| | | |
|---|---|---|
| WO | WO 00/03747 | 1/2000 |

* cited by examiner

*Primary Examiner*—David M. Naff
(74) *Attorney, Agent, or Firm*—Crowell & Moring LLP

(57) ABSTRACT

The present invention relates to a nano-calcium phosphates/collagen composite that mimics the natural bone, both in composition and microstructure, as well as porous bone substitute and tissue engineering scaffolds made by a complex of said composite and poly(lactic acid)(PLA) or poly (lactic acid-co-glycolic acid)(PLGA). The invention also relates to the use of said scaffold in treating bone defect and bone fracture.

10 Claims, 2 Drawing Sheets

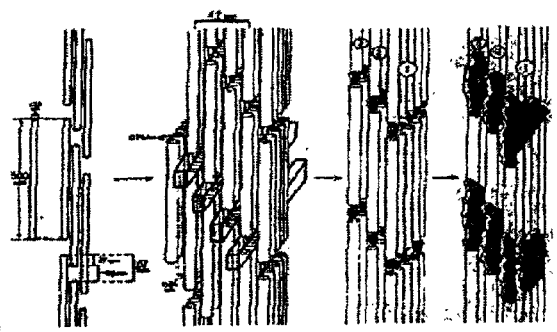
FIGURE 1A  FIGURE 1B
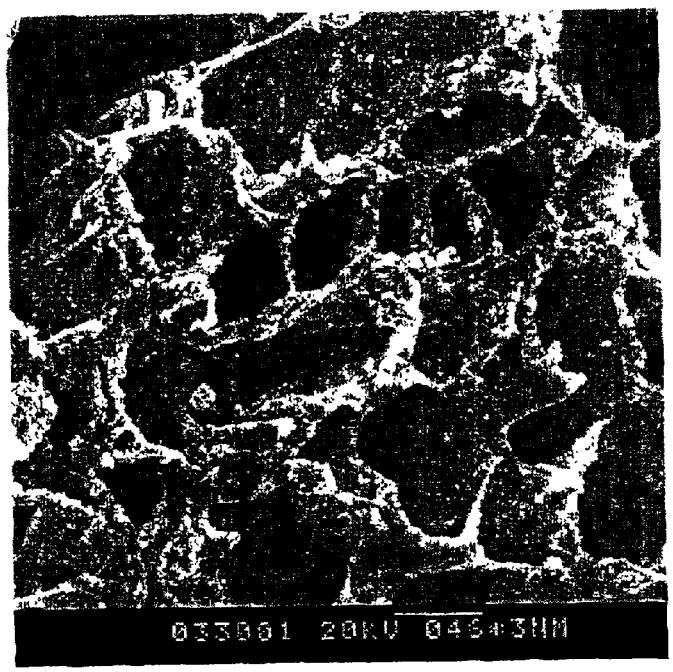
FIGURE 2

Postoperation　　　　24 weeks after operation

NANO-CALCIUM PHOSPHATES/COLLAGEN BASED BONE SUBSTITUTE MATERIALS

FIELD OF INVENTION

The present invention relates in general to bone substitute materials, and particularly to a nano-calcium phosphates/collagen composite that mimics the natural bone, both in composition and microstructure, as well as porous bone substitute and tissue engineering scaffolds made by a complex of said composite and poly(lactic acid) or poly(lactic acid-co-glycolic acid). Used as biodegradable bone substitute materials, the porous scaffold is capable of supporting and encouraging bone growth into its pores, and it is finally biodegraded with the formation of new bone.

BACKGROUND OF THE INVENTION

Bone repair is a subject of intensive investigation in human health care. Current therapy in bone reconstructive surgery frequently uses autograft or allograft although restrictions on these bone transplants exist. These restrictions include donor site morbidity and donor shortage for autograft (Pross R, editor. Orthop Knowledge Update 1990;3; Damien J C et al J Appl Biomater 1991;2:187–208.) and immunologic response and risk of transmitting diseases for allograft (Pross R, editor. Orthop Knowledge Update 1990:3; Binderman I et al, CRC Handbook of Bioactive Ceramics. Boca Raton, Fla.: CRC Press; 1990. p45–51). Heretofore, numerous bone substitutes using metals, ceramics, and polymers have been developed. However, each has specific disadvantages, and none of them can take the places of autograft and allograft in current clinical practice. One important reason for the priority of autograft and allograft is that their composition and microstructure are the same as the bone to be repaired therefore possess biological advantages. Under the principles of tissue engineering, a material, which has similar composition and microstructure with natural bone, is expected to be a promising biological substitute for regenerating, replacing, or enhancing tissue function.

It has been known that natural bone is a complex biomineralized system with an intricate hierarchial structure. Collagen and calcium phosphate minerals are the main substances existed in bone. The calcium phosphate minerals in bone exist as irregularly shaped mineral platelets, whose crystallographic c-axes are oriented generally parallel to one another. The crystal width varies (30–45 nm) but crystal thickness is uniform (~4–6 nm). Adjacent platelets are spatially separated by a layer of collagen whose thickness is 4.2±1.0 nm in minimum (W. J. Landis et al, J Structure Biology 110,39–54(1993)). The finely aligned collagen, which exists as a most important extracellular matrix, is a key factor influencing cell activities.

Except the composition and microstructure of natural bone the interconnecting porous structure of natural bone also play an important role in nutrient transportation and ingrowth of new bone.

In order to take the roles played by autograft and allograft, bone substitute materials made under the principle of biomimetic strategy, and which mimic the natural bone both in composition and microstructure, are still in great demand.

Thus, one of the objects of this invention is to provide a nano-calcium phosphates/collagen composite that mimics the natural bone, both in composition and microstructure so as to be used in the manufacture of bone substitute materials.

Another object of this invention is to provide porous bone substitute and tissue engineering scaffolds having excellent biocompatibility and biodegradability, which promote bone repair and regeneration. Said porous scaffolds are made by a complex of the nano-calcium phosphates/collagen composite and poly(lactic acid) or poly(lactic acid-co-glycolic acid).

SUMMARY OF THE INVENTION

According to one aspect, the invention provides a nano-calcium phosphates/collagen composite comprising collagen molecules and nano-calcium phosphates. Said composite in microstructure level is agglomerated particles having a diameter of 5–50 microns. And in nanostructure level the composite is of multiple laminar structure having periodic repeated units, and each periodic repeated unit has a thickness of 10–15 nm and consists of a layer of nano-calcium phosphates and a layer of collagen.

The invention also relates to a process for preparing the composite of the invention, which process comprises the following steps:

(a) dissolving collagen gel in acetic acid, then adding aqueous solutions of sodium phosphate and $CaCl_2.6H_2O$, wherein the weight ratio of Ca:P is between 1:1 to 1.67:1, and the amounts of collagen and minerals used are corresponding to those in the natural bone;

(b) adding in drops sodium hydroxide solution until the calcium phosphates start to co-precipitate with collagen;

(c) maintaining the solution of step (b) at neutral pH and incubating the solution at 30° C. for 1~5 days; and (d) harvesting the composite by centrifugation, freeze-drying and grinding into fine powder.

According to another aspect, the invention provides a porous bone substitute and tissue engineering scaffold. Said scaffold comprises a complex of the composite of the invention and poly(lactic acid)(PLA) and poly(lactic acid-co-glycolic acid)(PLGA), wherein the porosity of the scaffold is over 70%, the pore size is 100–500 microns and the weight ratio of said composite and poly(lactic acid)(PLA) or poly(lactic acid-co-glycolic acid)(PLGA) is between 3:7 to 1:1.

According to still another aspect, the invention provides a process for preparing the porous bone substitute and tissue engineering scaffold, comprising the following steps:

(a) dissolving poly(lactic acid) or poly(lactic acid-co-glycolic acid) in dioxane to a final concentration of 2.5–15% (w/v), then stirring the solution gently for 4 to 6 hours;

(b) adding the nano-calcium phosphates/collagen composite powder of the invention with the ratio of composite: poly(lactic acid) or poly(lactic acid-co-glycolic acid) being 3:7 to 1:1;

(c) ultrasonicating the solution of step (b), then pouring into a mould and freezing at a temperature between 0 to −20° C. overnight; and (d) transferring the frozen molded scaffold into a freeze drying machine to remove dioxane crystals.

DETAILED DESCRIPTION OF THE INVENTION

In order to fully understand the invention, the following definition is given:

The term of calcium phosphates used herein is meant minerals such as hydroxyapatite(HAP), dicalcium phosphate dihydrate (DCPD), ocatacalcium phosphate (OCP) and the like, which exist in natural bone.

Natural bone is a complex biomineralized system with an intricate hierarchical structure (Park J B et al, Biomaterials an introduction. New York: Plenum; 1992. chap.4). It is assembled through the orderly deposition of calcium phosphates within a type I collagenous organic matrix. Bone mineral that comprises approximately 60–70% of the total dry bone weight is nonstoichiometric apatite with low crystallinity and nanometer size (Lowenstam H A et al, On biomineralization. New York: Oxford University Press; 1989. p.35–40; Landis W J et al, J Struct Biol 1993;110:39–54). The crystallographic c axis of the apatite is oriented to the axis of the collagen fibril (Landis W J et al, J Struct Biol 1993;110:39–54; Matsuchima N et al, Jpn J Appl Phys 1982;21:186–189). The unique characteristics of bone mineral make it different from the sintered hydroxyapatite ceramic in many properties such as the binding state with the organic matrix and biodegradability. The preferential orientation of bone minerals and the interfacial bonding between the mineral and organic constituents play an important role in determining the overall mechanical behavior of bone (Walsh W R et al, Ann Biomed Eng 1994;22:404–414; Walsh W R et al, J mater Sci Mater Med 1994;5:72–79; Bundy K J, Ann Biomed Eng 1985;13:119–135). Furthermore, the assembly of the minerals and matrix is accomplished in aqueous media at ambient conditions.

The nano-calcium phosphates/collagen composite of the invention mimics the natural bone, both in composition and microstructure. The collagen matrix of the composite serves as template for mineral nucleation and growth. Calcium phosphates in nanometer scale are uniformly distributed on the matrix. FIG. 1B is a schematic illustration of the layer structure of natural bone. FIG. 1A is a transmission electron microscopic photo demonstrating the laminar property of the nano-calcium phosphates/collagen composite of the invention. As indicated by the arrows in FIG. 1A, the thickness of the one layer of calcium phosphates plus one layer of collagen is 11.7 nm. From these figures, it clearly demonstrates that the composite of the invention indeed mimics the natural bone in microstructure.

Numerous works on bioactive ceramics, glasses, or glass-ceramics have indicated that in vivo formation of Ca—P-rich layer and surface bone-like calcium phosphates is the key step in the bone-bonding behavior of these materials (Tracy B M et al, J Biomed Mater Res 1984; 18:719–726; Gross U et al, J Biomed Mater Res 1985; 19:251–271) Neo M et al, J Biomed Mater Res 1993;27:999–1006). Thus, the above-mentioned features give the composite of the invention bone-bonding ability. On the other hand, the low crystallinity of the minerals in the composite is of importance for their remolding in vivo. In addition, collagen and nano-calcium phosphates possess a highly effective affinity for various factors that in turn regulate cell function and promote events in osteogenesis. So the composite of the invention is similar to natural bone in component, microstructure.

In the nano-calcium phosphates/collagen composite of the invention, the collagen is type I. The weight ratio of nano-calcium phosphates to collagen molecules is between 2.2 to 2.8, which is similar to the natural bone.

According to another aspect, the invention provides a process for preparing the composite of the invention. It is known that collagen is a structural protein with good performance in maintaining bone mechanical integrity. With the collagen being assembled properly (like in the natural bone) with osteoinductive inorganic calcium phosphates such as hydroxyapatite, the composite of the invention has demonstrated excellent tenacity, toughness, biocompatibility and bioactivity. The process of the invention is accomplished under the idea of bio-self-assembling, that is, in the present process, calcium phosphates are formed in situ and deposited on the template of acid dissolved collagen. To this end, collagen is dissolved in acetic acid and aqueous solutions of sodium phosphate and $CaCl_2.6H_2O$ are then added. When the pH value increases from about pH2 to pH 7 to 8, the acid-dissolved collagen assembles into fibers on which the $Ca^{2+}$, $PO_4^{3-}$ ions begin to deposit. Then, the solution is maintained at neutral pH and incubated at 30° for 1 to 5 days before finally the composite is harvested by centrifiigation. In this way, collagen and calcium phosphates are integrated as a whole in the composite of the invention. The calcium phosphates are of low crystallinity. And the phase composition is controlled by parameters such as the Ca/P ratio of starting materials and time of incubation. Higher Ca/P ratio and longer incubation time generally lead to more HAP content in the final composite. At the Ca/P of 1.67 and 5 days incubation the calcium phosphates in the final composite are mainly hydroxyapatite.

During the formation of calcium phosphates crystals the temperature shall never be above 37° C. otherwise the product will mainly be needle-like calcium phosphates crystals rather than laminar calcium phosphates.

According to yet another aspect of the invention, there provides a porous bone substitute and tissue engineering scaffold made by a complex of the composite of the invention and poly(lactic acid) or poly(lactic acid-co-glycolic acid). In the complex the nano-calcium phosphates/collagen composite is added as an osteoinductive component. Different from ceramic this component has demonstrated much better bioactivity for its nano-sized lamellar property and can be biodegraded totally within an acceptable period.

The scaffold disclosed herein is an implantable bone substitute material and it is a complex of poly(lactic acid) or poly(lactic acid-co-glycolic acid) and nano-calcium phosphates/collagen composite. The porosity of the scaffold is over 70% and the pore size is 100–500 microns. The weight ratio of said composite and poly(lactic acid) or poly(lactic acid-co-glycolic acid) is between 3:7 to 1:1. By adjusting the content of the PLA or PLGA, scaffolds with different mechanical properties can be obtained. Scaffolds with higher PLA or PLGA contents can be used as bone substitute materials, and scaffolds with lower PLA or PLGA contents can be used in tissue engineering for culturing cells. FIGS. 2 and 3 are scanning electron microscopic photos showing the scaffolds of the invention for bone substitute and tissue engineering, respectively. From FIG. 2, it can be seen that the scaffold of the invention has interconnecting pores that are similar with those of the natural bone.

The scaffold is an osteoconductive and osteoinductive system. The osteoinductive part is the composite and the osteoconductive part is the porous polymer scaffold, which also provides the mechanical support. The scaffold has an interconnecting porous structure and a controllable porosity which is over 70%, especially between 70%–90%. Compared to ceramic, the scaffold of the invention is more flexible to adapt to environmental changes during bone formation. The pore size is in the range of 100–500 microns, thus providing a large surface area for cell attachment and sufficient space for nutrient transportation, vascular invasion, and bone ingrowth. The porous structure of the scaffold could further promote the adsorption and concentration of signal molecules on and within the composite. Once combined with noncollagenous bone matrix proteins, such as bone morphogenetic protein (BMP) and various bone growth factors (BGF) as well as multiple glycoproteins that can promote cell attachment and spreading, the scaffold of the invention will promote bone forming process in a great deal. With the porous structure of the scaffold of the invention, the noncollagenous bone matrix proteins or bone growth factors (BGF) can be released slowly so as to take effect. And because the degradation products of poly(lactic acid) or poly(lactic acid-co-glycolic acid) are low molecular weight compounds, such as lactic acid, glycolic acid, which enter into normal metabolic pathways, the scaffold are totally biodegradable and even the degradation rate can be adjusted by using poly(lactic acid) or poly(lactic acid-co-glycolic acid) of different molecular weight.

According to yet another aspect, the invention provides a process for preparing a porous bone substitute and tissue engineering scaffold. In the process, dioxane is used as solvent to process the poly(lactic acid) or poly(lactic acid-co-glycolic acid). Dioxane is chosen because it is not only a good solvent of poly(lactic acid) or poly(lactic acid-co-glycolic acid) but also a good pore former. By changing the temperature of dioxane crystallization, the pore size formed can be controlled, the lower the temperature, the smaller the pore size is. When the temperature is decreased from room temperature to the temperature below the melting point (approx. 11.8° C.) of dioxane, dioxane begin to crystallize, occupying spaces which will be the pores after the dioxane crystals are removed. When the crystallization of dioxane takes place, the solutes of poly(lactic acid)or poly(lactic acid-co-glycolic acid) are propelled to the front of the dioxane crystals. Then two separated phases of the dioxane crystals and the poly(lactic acid) or poly(lactic acid-co-glycolic acid) are formed. The crystals of dioxane can be removed by freeze drying, leaving the occupied spaces as uniformly distributed and interconnected pores.

In contrast, many methods in the art for making pores, such as salt leaching (U.S. Pat. No. 5,626,861) or heat induced decomposition of some bubble making composite, have their shortcomes. For example the latter has some difficulty in controlling the pore size or the interconnectivity of pores and salt leaching method need to remove solvent and solute from the scaffold respectively. In the present process, dioxane is used not only as a solvent but also a pore former, thus avoiding the difficulty in salt leaching method, and morphology or size will be more controllable in the present process.

Another advantage of the present process is the utilization of poly(lactic acid) or poly(lactic acid-co-glycolic acid). These polymers offer distinct advantages in that their sterilizability and relative biocompatibility have been well documented. In addition, their degradation rates can be tailored to match that of new tissue formation. And their degradation products are low molecular weight compounds, such as lactic acid and glycolic acid, which enter into normal metabolic pathways. By using PLA or PLGA of different molecular weight scaffold with different mechanical properties can be obtained. Higher molecular weight generally makes stronger scaffold.

BRIEF DESCRIPTION OF THE DRAWINGS

FIG. 1A is a transmission electron microscopic photo demonstrating the laminar property of the nano-calcium phosphates/collagen composite of the invention. FIG. 1B is a schematic illustration of the layer structure of natural bone.

FIG. 2 is scanning electron microscopic section image of the bone substitute scaffold of the invention showing the interconnected properties of the pores.

Figure 3:
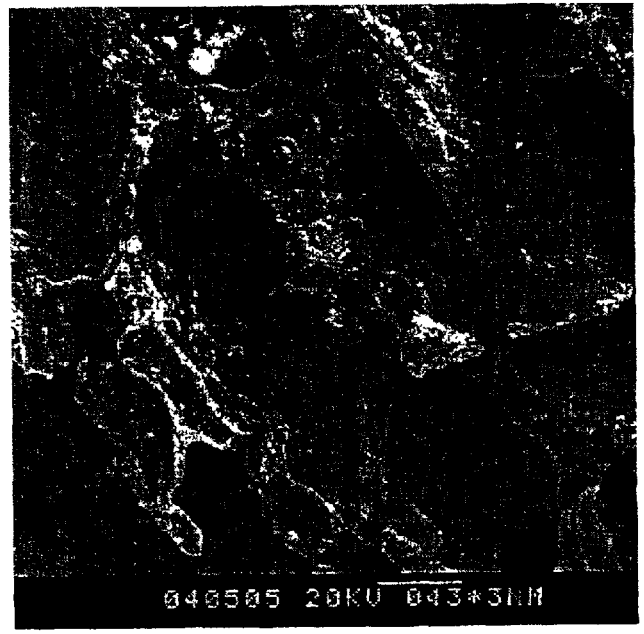
FIG. 3 is a scanning electron microscopic photo of bone tissue engineering scaffold of the invention.

The invention will be explained in detail by the following non-limited examples. Unless otherwise indicated, all the materials and reagents used in the examples are purchased from Chemical Agents Co. Ltd Beijing China.

EXAMPLE 1

Preparation of Nano-calcium Phosphates/collagen Composite 2 g type I collagen gel (1%) was dissolved in 30 ml 0.5M acetic acid. 11 ml of 0.1 mol/l $Na_2HPO_4$ and 18.3 ml of 0.1 mol/l $CaCl_2.6H_2O$ were then added. The resultant solution was gently stirred at room temperature, and 0.5M sodium hydroxide solution was added in drops to adjust the pH to 7.4. With the increase of pH value, the solution became supersaturated gradually and calcium phosphates started to precipitate with collagen. The solution was maintained at pH 7.4 for 48 hours, after which the product was harvested by centrifugation at 5000 rpm. The product was then freeze dried and ground into fine powder, thus the composite was obtained.

EXAMPLE 2

Preparation of Bone Substitute Scaffolds

Dissolve PLA in dioxane and stir the solution at a temperature of 30° C. for 4 hours then add the prepared powder of Example 1 into the solution slowly. Several different ratios of PLA to nano-calcium phosphates/collagen composite powder were used, which are listed in Table 1. The mixed solution is treated with ultrasonic system (KQ-50B, Kunshan Co. Ltd, Beijing China) for 5 minutes to distribute the composite powder uniformly. Pour the resultant solution into a pre-shaped mould, which is made of Teflon, and freeze at 0° C. overnight. The frozen mould is then transferred into a freeze-drying machine (Alpha 1–2, Martin CHRIST Co. Ltd, Germany) for 72 hours to remove the dioxane crystals. The final products are strong scaffolds suitable for bone substitute.

TABLE 1

Start materials for the preparation of bone substitute materials

| | |
|---|---|
| A Nano-calcium phosphate/collagen powder | 0.3 g |
| PLA (MW 100,000) | 0.7 g |
| Dioxane | 6 ml |
| B Nano-calcium phosphate/collagen powder | 1 g |
| PLA (MW 150,000) | 1 g |
| Dioxane | 10 ml |
| C Nano-calcium phosphate/collagen powder | 0.4 g |
| PLA (MW 100,000) | 0.6 g |
| Dioxane | 6 ml |
| D Nano-calcium phosphate/collagen powder | 0.4 g |
| PLA (MW 80,000) | 0.6 g |
| Dioxane | 6 ml |
| E Nano-calcium phosphate/collagen powder | 0.93 g |
| PLA (MW 50,000) | 1.4 g |
| Dioxane | 10 ml |

EXAMPLE 3

Scaffolds for Used as Tissue Engineering Substitutes

Scaffolds of varying porosity and pore size were fabricated using the process of Example 2 and the start materials as listed in Table 2. The concentration of dissolving PLA in dioxane is 2.5% and 5%, respectively. The weight ratio of PLA to Nano-calcium phosphate/collagen composite is about 2:1. The solution is frozen at about −10° C. The obtained products possess an even higher porosity and bigger pore size, porosity is above 90% and pore size above 150 micrometer, both of these make the scaffold more suitable for tissue engineering by promoting cell activities such as cell migration and proliferation.

TABLE 2

Start materials for the preparation of tissue engineering substitutes

| | | |
|---|---|---|
| A | Nano-calcium phosphate/collagen powder | 0.125 g |
| | PLA (MW 80,000) | 0.25 g |
| | Dioxane | 10 ml |
| B | Nano-calcium phosphate/collagen powder | 0.25 g |
| | PLA (MW 100,000) | 0.5 g |
| | Dioxane | 10 ml |
| C | Nano-calcium phosphate/collagen powder | 0.25 g |
| | PLA (MW 40,000) | 0.5 g |
| | Dioxane | 10 ml |

EXAMPLE 4

Testing the Biocompatibility and Bioactivity of the Scaffold

The scaffold prepared by formula B of Example 2 was implanted into the Latissimus dorsi tissue of rabbit (obtained from The Fourth Medical University, Xian China). Four weeks later blood vessel and ingrowth of connective tissue were seen, with no lymphocyte or foreign body giant cell. This result demonstrated the good biocompatibility of this scaffold.

EXAMPLE 5

Animal Experiments

The scaffold prepared by formula B of Example 2 was used to fix a 15 mm segmental wound in radius bone of 16 rabbits (obtained from The Fourth Medical University, Xian China). After 12 weeks the rabbits were sacrificed to see the result. All of the wounded places healed well, no infection was seen.

Figure 4:
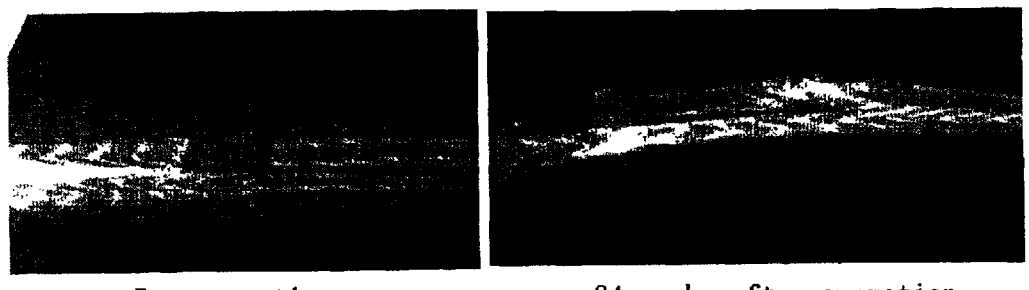
FIG. 4 is an X-ray image demonstrating the effectiveness of the scaffold of the invention in bone repair.

The scaffold prepared by formula A of Example 2 was used to fix a 20 mm segmental wound in radius bone of dogs (obtained from The Fourth Medical University, Xian China). RhBMP-2 was added to increase its bioactivity. 12 weeks after the operation the wound healed completely. FIG. 4 is the x-ray image of this experiment.

What is claimed is:

1. A nano-calcium phosphate/collagen composite, comprising collagen molecules and nano-calcium phosphate, wherein said composite comprises agglomerated particles having a diameter of 5–50 microns, wherein the agglomerated particles comprise a multiple laminar structure having periodically repeated units, each periodically repeated unit having a thickness of 10–15 nm and consisting of a layer of calcium phosphates and a layer of collagen.

2. The nano-calcium phosphates/collagen composite of claim 1, wherein the collagen is type I collagen.

3. The nano-calcium phosphates/collagen composite of claim 1, wherein the weight ratio of nano-calcium phosphates to collagen molecules is between about 2.2 to about 2.8.

4. A process for preparing the composite of claim 1, comprising the following steps:

(a) dissolving collagen gel in acetic acid, then adding aqueous solutions of sodium phosphate and calcium chloride, wherein the weight ratio of Ca:P is between 1:1 to 1.67:1;

(b) adding in drops sodium hydroxide solution until the calcium phosphates start to co-precipitate with collagen;

(c) maintaining the solution of step (b) at a neutral pH and incubating the solution at 30° C. for 1~5 days; and (d) harvesting the composite by centrifugation, freeze-drying and grinding into fine powder.

5. A porous scaffold for use as a bone substitute or in tissue engineering, comprising a complex of the composite of claim 1 and poly(lactic acid) or poly(lactic acid-co-glycolic acid), wherein the weight ratio of said composite and poly(lactic acid) or poly(lactic acid-co-glycolic acid) is between about 3:7 to about 1:1, the porosity is about 70% or more and the pore size is about 100–500 microns.

6. The scaffold of claim 5, further comprising noncollagenous bone matrix proteins selected from the group consisting of bone morphogenetic protein, bone growth factors and glycoproteins that can promote cell attachment and spreading.

7. A process for preparing a porous scaffold for use as a bone substitute or in tissue engineering, comprising the following steps:

(a) dissolving poly(lactic acid) or poly(lactic acid-co-glycolic acid) in dioxane to a final concentration of about 2.5–15%(w/v), then stirring the solution gently for about 4 to 6 hours;

(b) adding the nano-calcium phosphate/collagen composite powder of claim 1 with a ratio of composite: poly(lactic acid) or poly(lactic acid-co-glycolic acid) of about 3:7 to 1:1;

(c) ultrasonicating the solution of step (b), then pouring the solution into a mold and freezing at a temperature between 0 to −20° C. overnight; and (d) transferring the frozen molded solution into a freeze drying machine to remove dioxane to obtain said scaffold.

8. A porous scaffold obtained by the process of claim 7.

9. A method of treating bone defect or bone fracture, said method comprising administering to said bone defect or bone fracture an effective amount of a scaffold according to claim 5, 6 or 8.

10. A method of culturing osteocytes, said method comprising providing an effective amount of a scaffold according to claim 5, 6 or 8 for culturing osteocytes.

* * * * *